(12) United States Patent
Feinbloom et al.

(10) Patent No.: US 7,883,233 B2
(45) Date of Patent: *Feb. 8, 2011

(54) ILLUMINATION ASSEMBLY

(75) Inventors: Richard Feinbloom, New York, NY (US); Kenneth Braganca, Floral Park, NY (US); Peter Yan, Rego Park, NY (US)

(73) Assignee: Designs for Vision, Inc., Ronkonkoma, NY (US)

( * ) Notice: Subject to any disclaimer, the term of this patent is extended or adjusted under 35 U.S.C. 154(b) by 256 days.

This patent is subject to a terminal disclaimer.

(21) Appl. No.: 11/975,194

(22) Filed: Oct. 18, 2007

(65) Prior Publication Data

US 2009/0116225 A1    May 7, 2009

(51) Int. Cl.
*F21L 4/00* (2006.01)
(52) U.S. Cl. .................. 362/105; 362/191; 362/190; 362/187; 362/106
(58) Field of Classification Search .................. 362/105, 362/184, 187, 190, 191, 106
See application file for complete search history.

(56) References Cited

U.S. PATENT DOCUMENTS

| 5,408,393 | A | * | 4/1995 | Becker | 362/105 |
| 5,440,462 | A | * | 8/1995 | Kim et al. | 362/105 |
| 5,722,762 | A | * | 3/1998 | Soll | 362/105 |
| 6,290,368 | B1 | * | 9/2001 | Lehrer | 362/187 |
| 6,390,640 | B1 | * | 5/2002 | Wong et al. | 362/105 |
| 6,461,024 | B1 | * | 10/2002 | Becker et al. | 362/331 |
| 6,877,875 | B2 | * | 4/2005 | Yu et al. | 362/105 |
| 6,955,444 | B2 | * | 10/2005 | Gupta | 362/105 |

* cited by examiner

*Primary Examiner*—Anabel M Ton
(74) *Attorney, Agent, or Firm*—Plevy & Keene LLP

(57) ABSTRACT

An assembly for providing illumination to a selected incident area includes a support; a first illumination device coupled to the support, the first illumination device including a first light emitting device and a first lens positioned for focusing light emitted by said first light emitting device; a second illumination device coupled to the support, the second illumination device including a second light emitting device and a second lens positioned for focusing light emitted by said second light emitting device; the first and second lenses projecting defocused images of the respective first and second light emitting devices to the selected incident area.

24 Claims, 14 Drawing Sheets

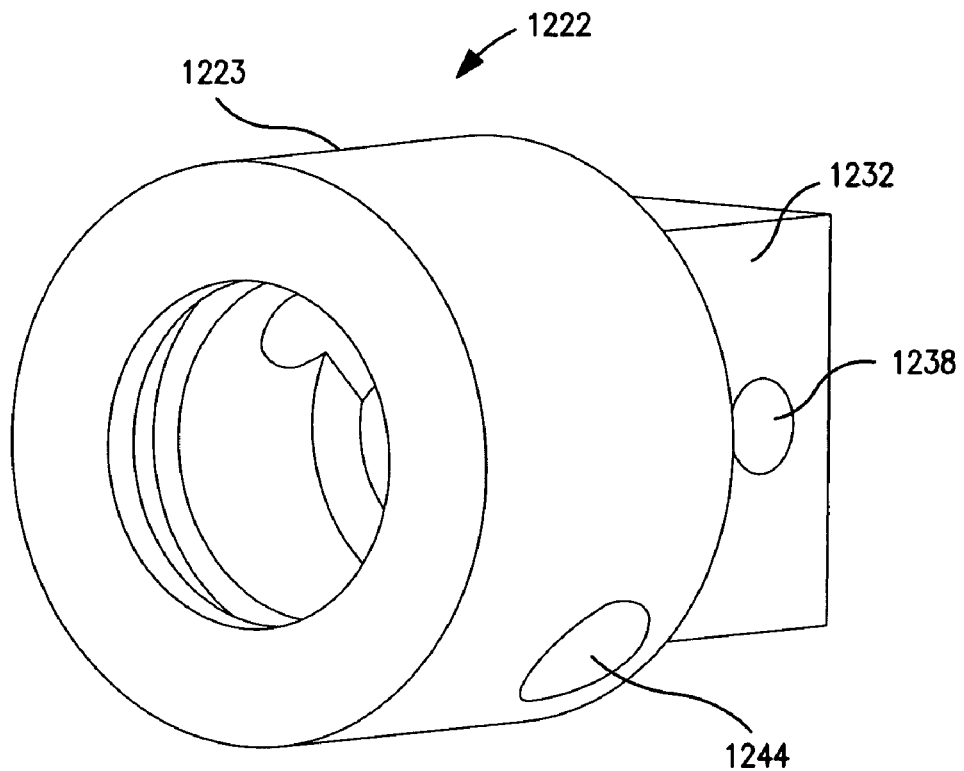
FIG. 12B
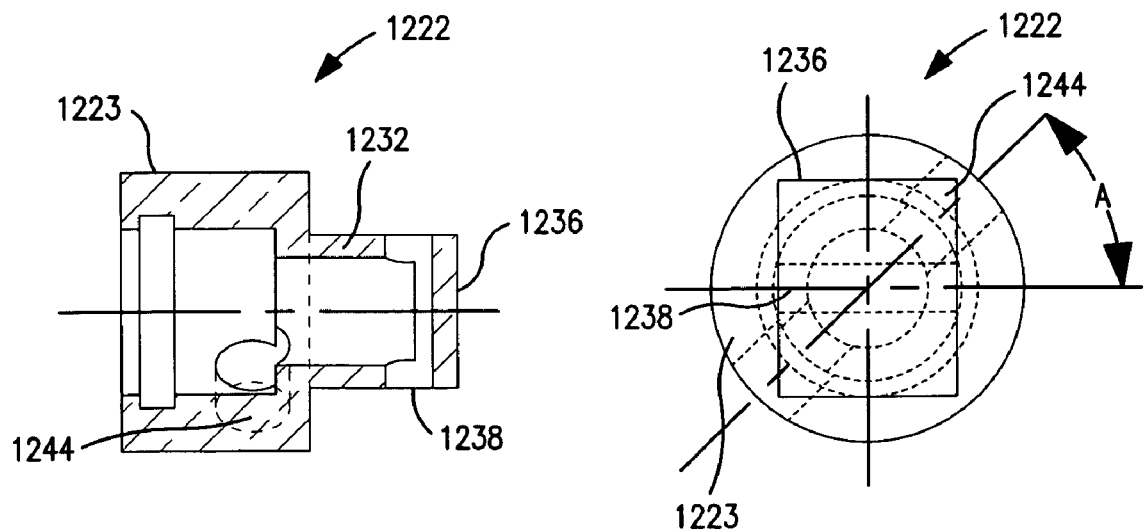
FIG. 12C  FIG. 12D

ILLUMINATION ASSEMBLY

FIELD OF THE INVENTION

This invention is in the field of illumination devices.

BACKGROUND

Illumination devices are employed in a wide variety of contexts. Various types of fine work require high intensity illumination over a small area a relatively short distance from the eyes of a user. Examples of such fine work include surgery and dentistry, as well as watch and jewelry repair. A relatively narrow beam is desirable for such applications. In other applications, illumination at a greater distance, or at a larger area, may be needed. Others who work at night or in areas lacking in illumination, such as rescue workers, miners, and utility workers, may require illumination at a greater distance, or over a larger area. Enhanced illumination may also be desirable in normal light conditions for persons having low vision.

One source of illumination is a light emitting diode. A commercial light emitting diode typically is in the form of a package having therein a die covered by a lens. The die typically includes an array of light emitting elements covered by a lens. Light is emitted by a typically commercial light emitting diode over a full semi-spherical range, with greater intensity in the forward direction. One device employed to provide a relatively narrow field of illumination is a collimator. An example of such a collimator is the Fraen Fiber Light Injector, from Fraen Corporation, of Reading, Mass. Such a collimator provides a beam which tends to diverge gradually.

SUMMARY OF THE INVENTION

An assembly for providing illumination to a selected incident area includes a support; a first illumination device coupled to the support, the first illumination device including a first light emitting device and a first lens positioned for focusing light emitted by said first light emitting device; a second illumination device coupled to the support, the second illumination device including a second light emitting device and a second lens positioned for focusing light emitted by said second light emitting device; the first and second lenses projecting defocused images of the respective first and second light emitting devices to the selected incident area.

A method of illuminating a target area a selected distance from an emitting device includes providing a first emitting array and a second emitting array. The method further includes projecting a defocused image of the first emitting array to the target area; and simultaneously projecting a defocused image of the second emitting array to the incident area.

A method of preparing an illumination assembly having at least one emitter array for illuminating a target area a selected distance from an output of the assembly includes projecting an image of the at least one emitter array through a focusing lens assembly to a surface at the selected distance; adjusting the lens assembly to focus the projected image; and adjusting the lens assembly to defocus the projected image.

BRIEF DESCRIPTION OF THE FIGURES

FIG. 12B is another view of the emitter mount of FIG. 12A.

FIG. 12C is a cross-section of the emitter mount of FIG. 12A.

FIG. 12D is a top view of the emitter mount of FIG. 12A, showing locations of bores therein.

DETAILED DESCRIPTION

Figure 1:
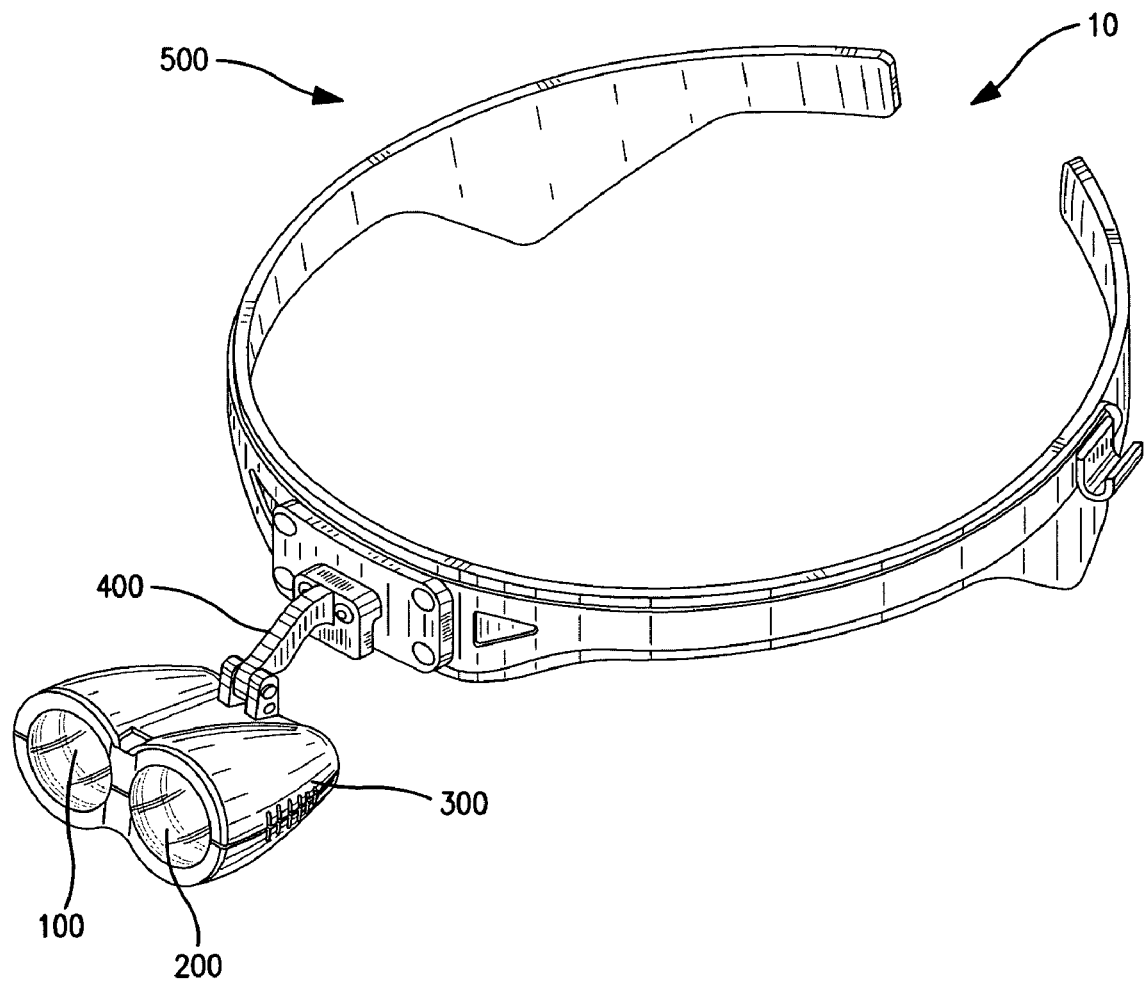
FIG. 1 is a perspective view of an illuminating assembly according to an embodiment of the invention.

Referring now to FIG. 1, an illuminating assembly 10 in accordance with an embodiment is illustrated. Assembly 10 includes generally two light-emitting units, or illumination devices, 100, 200, within housing 300. Illumination devices 100, 200 are both supported relative to one another within housing 300. Illumination devices 100, 200 are adapted to emit light in relatively narrow beams that intersect and entirely or substantially overlap a selected distance from the illumination devices. The selected distance at which the beams overlap may be selected depending on the particular application. For example, in applications such as surgery and dentistry, the relatively short distance may be, for example, between about 10 inches and about 30 inches, and more particularly between about 13 and about 24 inches, and about 13 inches, or about 16 inches, by way of example. In another example, in applications such as emergency workers, such as firefighters, the selected distance may be between about 2.5 feet and about 3 feet. In another example, in applications to assist persons with low vision, the selected distance may be between about 6 feet and about 8 feet. It will be appreciated that these are merely exemplary applications and selected distances. Headband 500 supports housing 300 including illumination devices 100, 200. Headband 500 may be adapted to fit about the head of a human user and support the assembly 10 thereon. Bracket 400 connects headband 500 and housing 300. Housing 300 is movably supported on bracket 400. Housing 300 serves as a support for illumination devices 100, 200.

Figure 2:
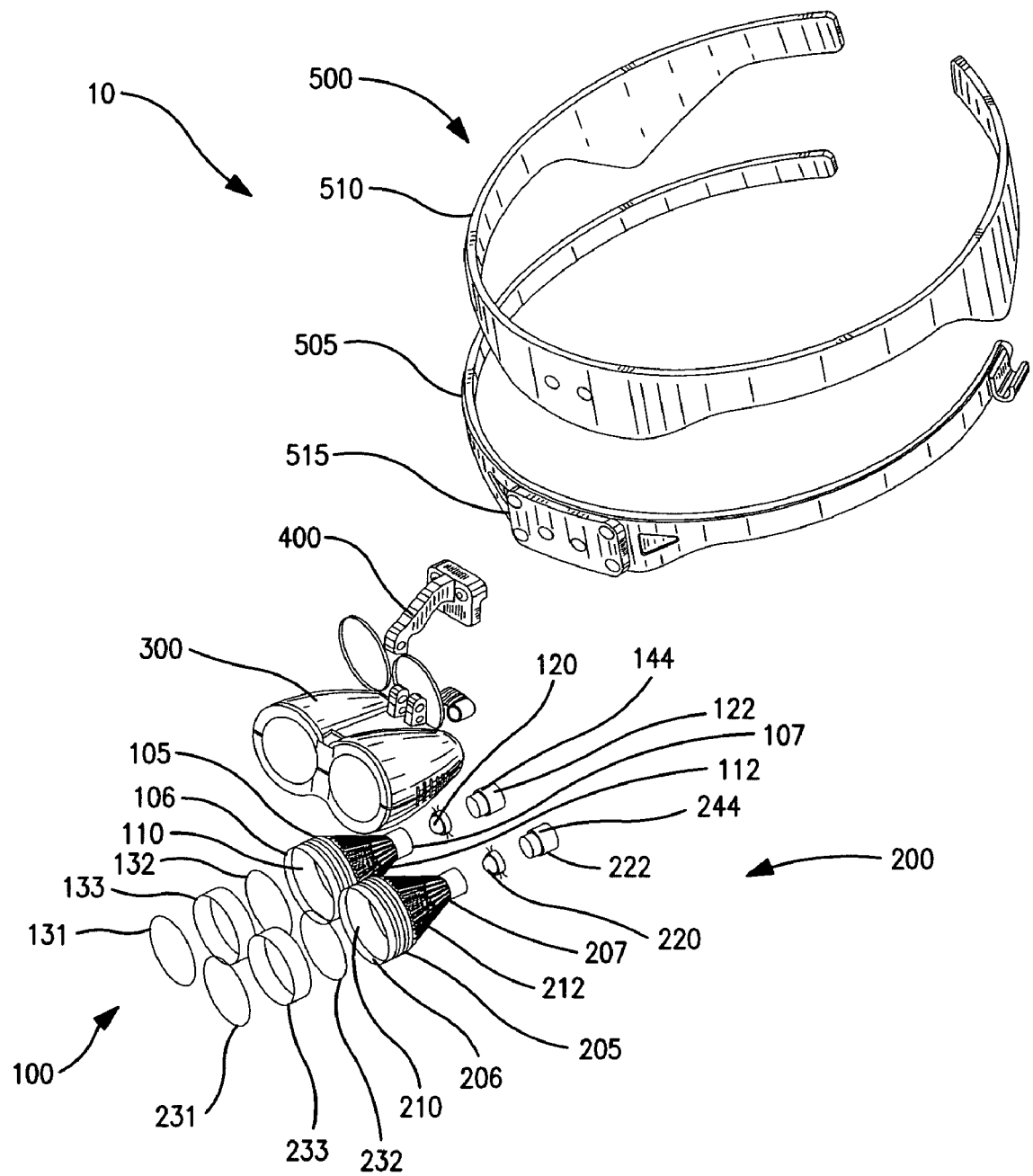
FIG. 2 is an exploded view of the illuminating assembly of FIG. 1.

Referring now to FIG. 2, an exploded view of assembly 10 is shown. Illumination device 100 includes an opaque housing 105 having a distal end 106 and a proximal end 107, an opening 110 at the distal end 106, and a tapering portion 112 intermediate the distal end 106 and the proximal end 107. An emitter 120, which may be a light emitting diode or an array of light emitting diodes is mounted in housing 105 near proximal end 107 and positioned to emit light toward opening 110.

Emitter 120 is mounted on emitter mount 122. Lenses 131, 132 are positioned in housing 105 distally of emitter 120 to receive and retransmit through opening 110 a portion of the emitted light. The relationship of the emitter 120, the emitter mount 122, and the housing 300 will be explained in greater detail below, with reference to FIGS. 7, 11, 12A, 12B, 12C and 12D.

Spacer 133 controls the positioning of lenses 131, 132. An O-ring and a closing ring may also be provided. The number and selection of lenses may be varied within the scope of the invention. For example, lenses 131, 132 may be spherical or aspheric, and may be of glass and with or without a plastic coating. Epoxy may be employed to fix lenses 131, 132 in spacer 133. More than two lenses may also be employed.

Figure 11:
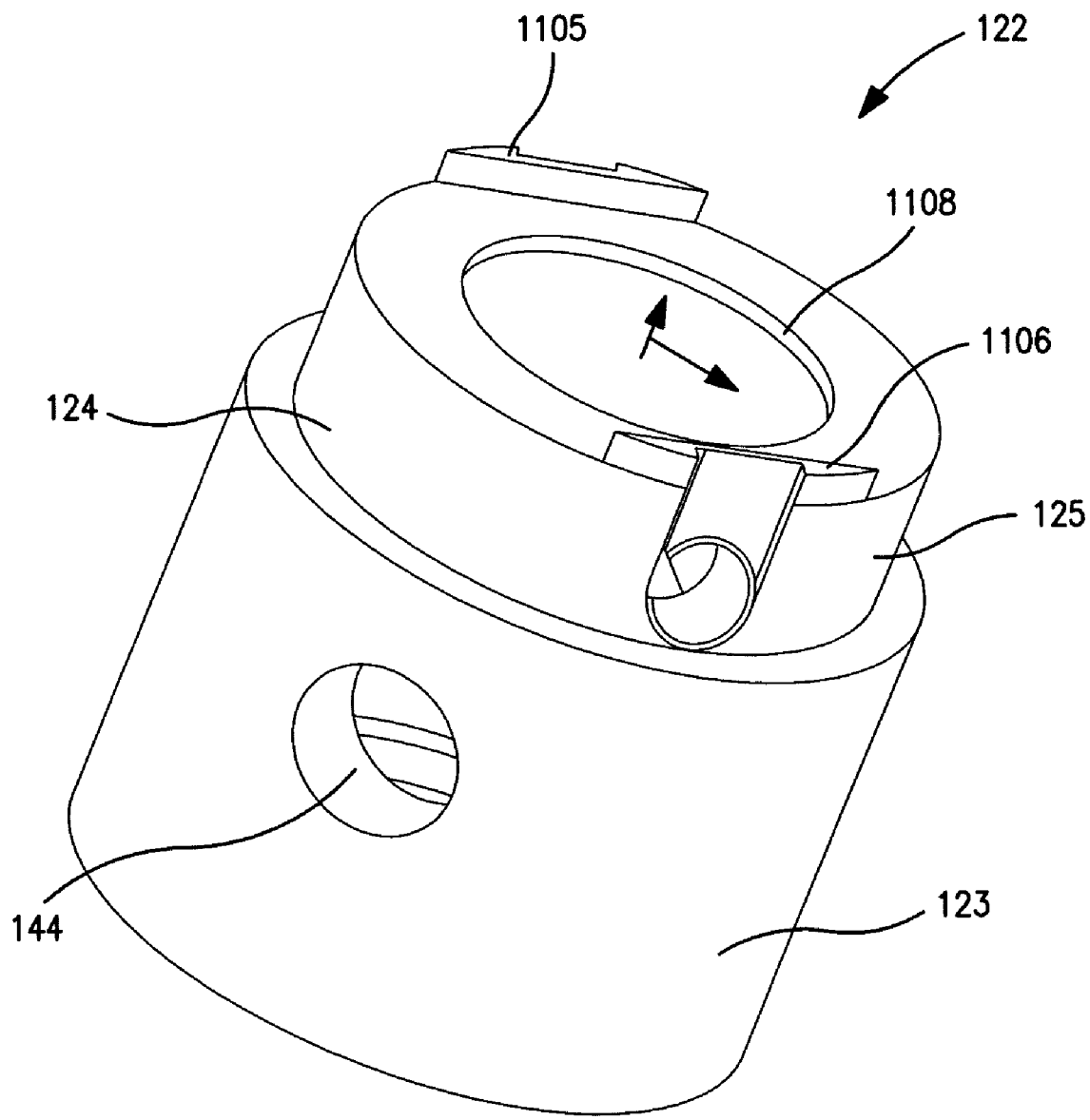
FIG. 11 is a view of an emitter mount for use in an assembly of FIG. 1.
Figure 12A:
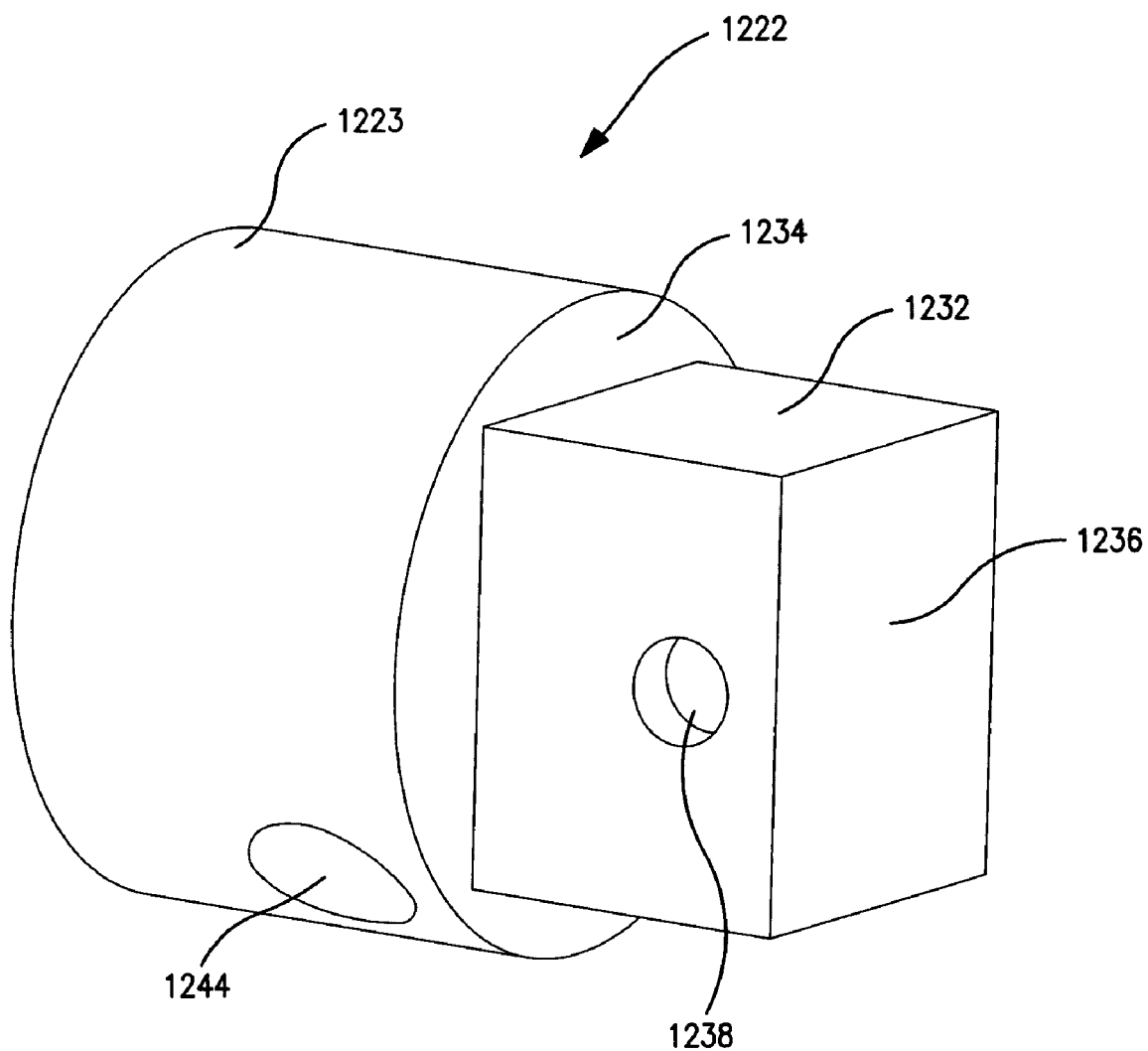
FIG. 12A is a view of an alternative emitter mount for use in an assembly of FIG. 1.

Emitter mount 122 may have a through bore 144 therethrough, which receives pins 321, 322 in housing 300, as described below with reference to FIG. 7. Referring again to FIG. 2, emitter mount 122 may be a good heat conductor, such as copper or a tellurium copper alloy, by way of example. Referring now to FIG. 11, emitter mount 122 is shown. Emitter mount 122 is generally a cylindrical, hollow body, closed at one end by wall 1108 to provide a platform for an emitter, and open at the other end. Major cylindrical wall 123 has a bore 144 through the center axis thereof, and a corresponding bore opposite thereto, to accommodate pins 321, 322 (shown in FIG. 7). Still referring to FIG. 11, emitter mount 122 has an end cylindrical wall 124, having bore 125, the central axis of which is through the central axis of end cylindrical wall 124 therein to accommodate wires for connection to an LED assembly. End cylindrical wall 124 is coaxial with, and of lesser diameter than, major cylindrical wall 123, and the two walls are joined by a shoulder. End wall 1108 has upstanding members 1105, 1106 at opposite sides, having parallel interior surfaces positioned to retain an LED at a selected orientation relative to bore 144. By way of example, the selected orientation may provide that an LED, such as LED 600 of FIG. 4, having a rectangular base, and a generally rectangular emitting array 605, the sides of the array 605 being parallel to the sides of the base, will be positioned so that the sides of the array are at an angle of about 45 degrees relative to the central axis of bore 144 and the bore opposite thereto through major wall 123. As a result of the vertical orientation of pins 321, 322 (shown in FIG. 7), the alignment of bore 144 through the central axis of emitter mount 122, and the angle between the axis of bore 144 and the sides of array 605 when mounted on emitter mount 122, a defocused image of array 605 will have a generally rectangular appearance, with sides being at about 45 degrees relative to horizontal.

Referring to FIGS. 12A, 12B, 12C and 12D, an alternative emitter mount 1222 is shown. Emitter mount 1222 may, similarly to emitter mount 122, be a good heat conductor, of copper or tellurium, for example. Emitter mount 1222 is generally in the form of a hollow body, open at one end, and closed at the other. Emitter mount 1222 has major cylindrical wall 1223 at its open end. Major cylindrical wall 1223 has bore 1244 through the central axis thereof. Bore 1244 may be adapted to receive pins 321, 322 of FIG. 7. Emitter mount 1222 has a generally rectangular hollow body 1232, having substantially planar side walls, and a rectangular end wall 1236 defining the closed end of emitter mount 1222. Hollow body 1232 is more narrow than major cylindrical wall 1223, and the two are joined by a shoulder 1234. Hollow body 1232 is centered on the axis of major cylindrical wall 1223. A bore 1238 through rectangular hollow body 1232 accommodates wiring to an emitter. End wall 1236 is so oriented as to accommodate an emitter at a specified orientation relative to bore 1244. In the illustrated example, as may be seen particularly in FIG. 12D, the sides of end wall 1236 are at angle of substantially 45 degrees relative to bore 1244. Similarly, bore 1238 in rectangular body 1236 is at angle A, which in the illustrated embodiment is 45 degrees, from bore 1244 in main cylindrical wall 1223.

It will also be appreciated that, in FIG. 11, end wall 1108 lies in a plane parallel to the axis of bore 144, of FIG. 11. Similarly, in FIG. 12, end wall 1236 lies in a plane parallel to the axis of bore 1244. Thus, end wall 1108 will be parallel to the common axis of pins 321, 322. Similarly, end wall 1236 will be parallel to the common axis of pins 321, 322. Emitter mount 122 may be configured so that end wall 1108 is positioned to be at a selected angle to the axis of bore 144, and thus at an angle to the axis of pins 321, 322. Similarly, emitter mount 1222 may be configured so that end wall 1236 is positioned at a selected angle to the axis of bore 1244, and to the common axis of pins 321, 322.

It will be appreciated that the emitter mounts of FIG. 11 and of FIGS. 12A, 12B, 12C and 12D may be mounted on pins 311, 312, which also have a common axis.

Referring again to FIG. 2, emitter mount 122 may be in physical contact with housing 105 or otherwise thermally coupled to housing 105, or configured to provide good heat conduction from emitter mount 122 to housing 105. Housing 105 may be made of a good heat conductor, such as copper or aluminum. Housing 105 may thereby serve as a heat sink. An uneven outer surface of housing 105 may be provided, such as by grooves defined in an outer surface of housing 105, to increase surface area and dissipate heat, although the particular configuration of such grooves depicted in the figures may have ornamental characteristics. Housing 105 may be machined from a single piece of material. Housing 105 may have a non-reflective interior surface.

Illumination device 200 may be identical to or similar to illumination device 100. Illumination device 200 has an opaque housing 205, which may be identical to opaque housing 105. Opaque housing 205 has a distal end 206 and a proximal end 207, with an opening 210 at the distal end 206. A tapering portion 212 may be provided intermediate distal end 206 and proximal end 207. Emitter 220, which may be a light emitting diode or an array of light emitting diodes, is mounted in housing 205 near proximal end 207 and positioned to emit light toward opening 210. Lenses 231, 232 are positioned in housing 205 distally of emitter 220 to receive a portion of the emitted light and to retransmit light through opening 210. Emitter 220 is mounted on emitter mount 222. Lenses 231, 232 are positioned in housing 205 distally of emitter 220 to receive and retransmit through opening 210 a portion of the emitted light. Lenses 231, 232 may be positioned by spacer 233. An O-ring and a closing ring may also be provided. The number and selection of lenses may be varied, as discussed above with respect to lenses 131, 132. Emitter mount 222 may be substantially identical to emitter mount 122 depicted in FIG. 11.

Headband 500 may include a supporting U-shaped member 505, which may be a strip of a material which provides inward tension to engage an object, such as a user's head, between the arms of the U. U-shaped member 505 may be of aluminum, or other lightweight, strong and flexible material, by way of example. A foam or fabric cushion 510 may be provided on an inside surface of U-shaped member 505, for the comfort of the user. A connecting plate 515, which may be of a lightweight rigid material, such as ABS, is secured to member 505 and provides for a connection to bracket 400.

Figure 7:
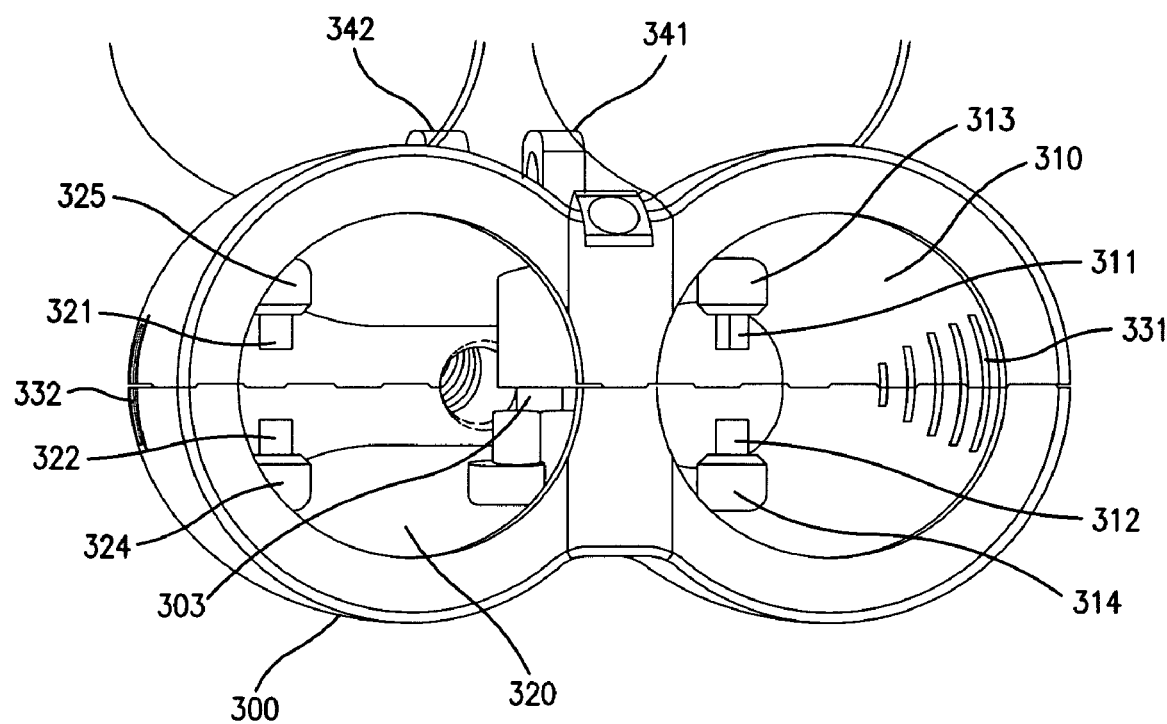
FIG. 7 is a view from the front of a housing of the illuminating assembly of FIG. 1.

Referring to FIG. 7, an enlarged view of housing 300, generally from the front, is provided. Housing 300 may include two hollow chambers 310, 320, each of which is open at the front thereof. Pins 311, 312 are disposed vertically in chamber 310 and aligned with one another. Pins 311, 312 are received in and protrude from bores in towers 313, 314. Pins 311, 312 are sized and positioned to be positioned in corresponding bore 144 in emitter mount 122, so as to engage the light emitting device 100. Pins 311, 312 may also be sized and positioned to be positioned in corresponding bore 1244 of emitter mount 1222 illustrated in FIGS. 12A, 12B, 12C and 12D, and described below.

Similarly, pins 321, 322 are disposed vertically in chamber 320 and aligned with one another. Pins 321, 322 are received in and protrude from bores in towers 324, 325. Pins 321, 322 are sized and positioned to be received in bore 144 in emitter mount 122 to engage light emitting device 100, or in bore 244 of emitter mount 222 (which may be identical to emitter mount 122 shown in FIG. 11), so as to engage light emitting device 200. Pins 321, 322 may also be sized and positioned to be positioned in corresponding bore 1244 of emitter mount 1222 illustrated in FIGS. 12A, 12B, 12C and 12D, and described below It will be appreciated that the positioning of emitter mounts 122, 222, including their separation from one another and their orientation on the axis defined by pins 311, 312, and on the axis defined by pins 321, 322, in housing 300 determines the angle of emission of light, and thus the distance at which the beams intersect. The distance at which the beams intersect may thus be selected by fixing the emitter mounts within a range of positions available by rotation of the emitter mounts about the pins. Advantageously, the same housing 300 and emitter mounts may be employed for different applications, by changing lensing, LED's, and angles of mounting. The distance at which the beams intersect is the selected distance for viewing. Alternatively, different emitter mounts, with differing angles between the closed end surface and the central axis of the bore, may be employed for different applications.

Referring now to FIG. 7, housing 300 may be made up of one piece, or of two or more pieces. In an embodiment, housing 300 may be made of generally symmetric upper and lower pieces, joined by a screw 303. Openings may be provided through the walls of housing 300 to provide air circulation around light emitting devices 100, 200. By way of example, such openings may be in the form of elongated vents 331, 332. Housing 300 may be of a lightweight, rigid plastic material, such as ABS.

Upstanding arms 341, 342 project upward from an upper surface of housing 300. Arms 341, 342 have bores which receive a shaft, as explained below with reference to FIG. 8.

Figure 3A:
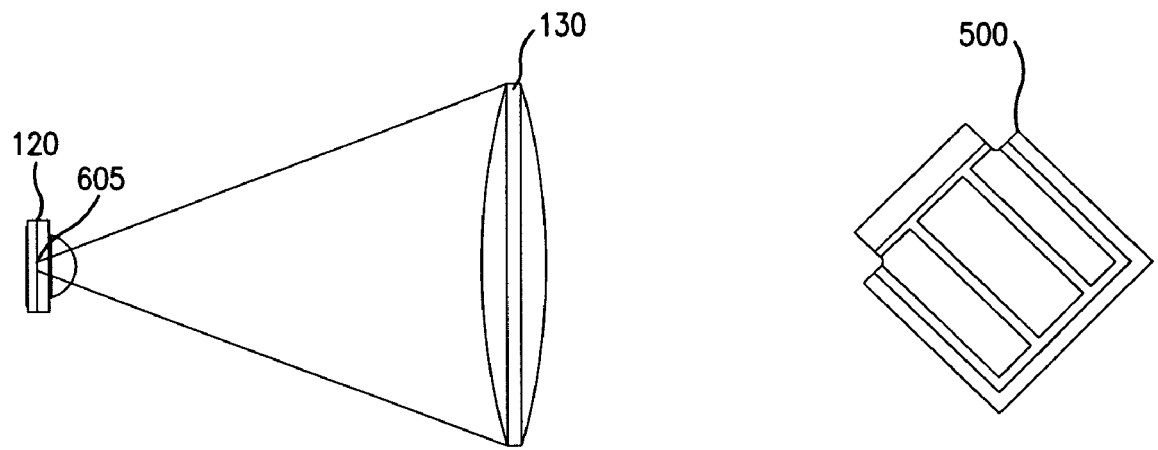
FIG. 3 is a simplified ray diagram of the illuminating assembly of FIG. 1.
Figure 3B:
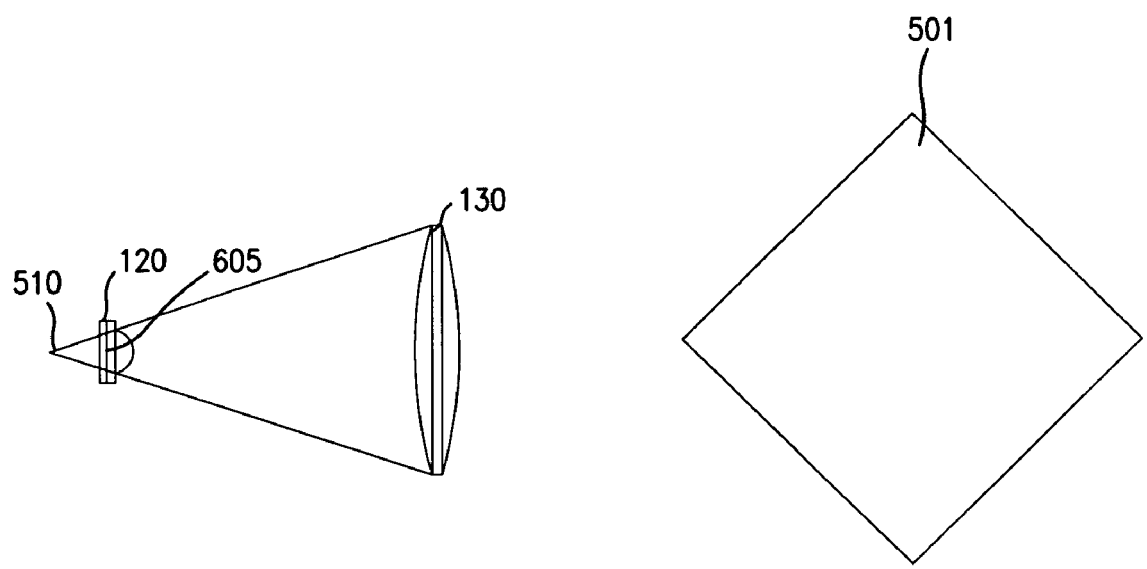
Figure 3C:
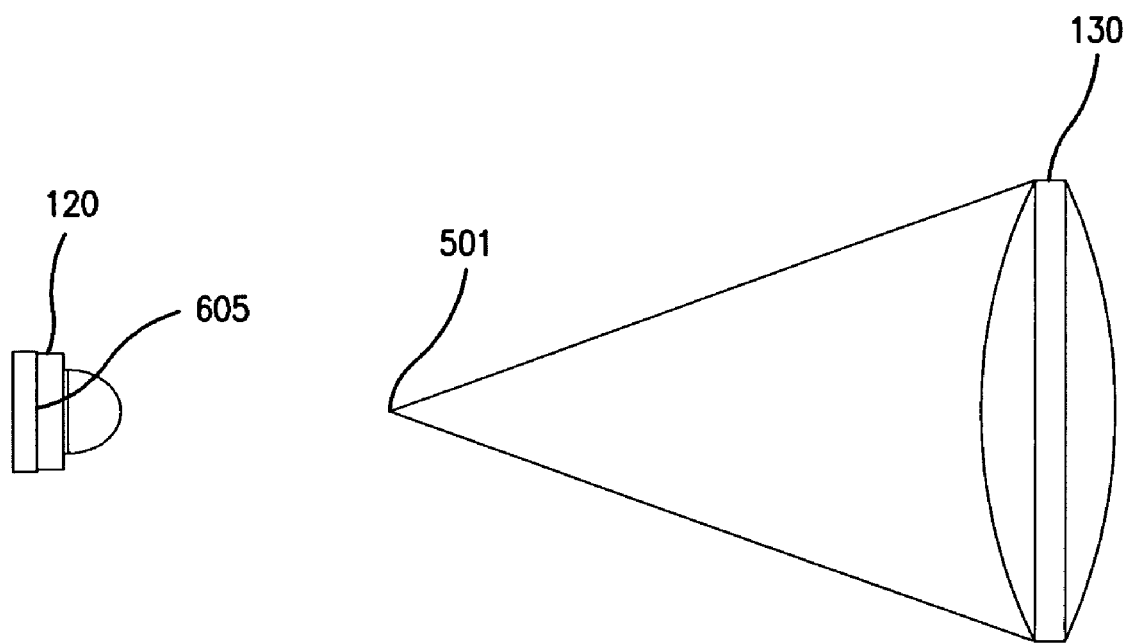

Referring to FIGS. 3A, 3B and 3C, somewhat schematic ray diagrams for an assembly of FIG. 2 are shown. Emitter 120 is shown in each view. Emitter 120 may be a light emitting diode having an array 605. Array 605 may have the pattern shown in FIG. 4. Referring to FIG. 3A, lensing 130 is positioned relative to array 605 with its focal point on array 605, so as to project an focused image 500 of array 605 on an incident area. Because of the pattern of array 605, this focused image 500 is undesirable. It will be appreciated that lensing 130 is merely schematic, and may include one, two or more lenses. In an embodiment, lensing 130 may include one or more reflectors.

Figure 9A:
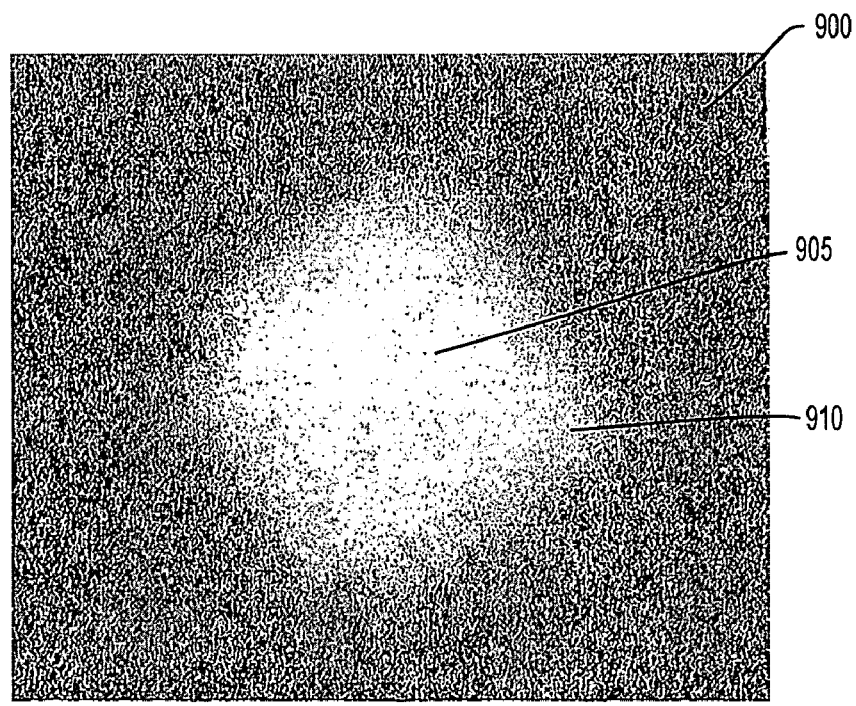
FIG. 9A is an image of an exemplary illuminated area showing a substantially in focus projected image of an emitting array.
Figure 9B:
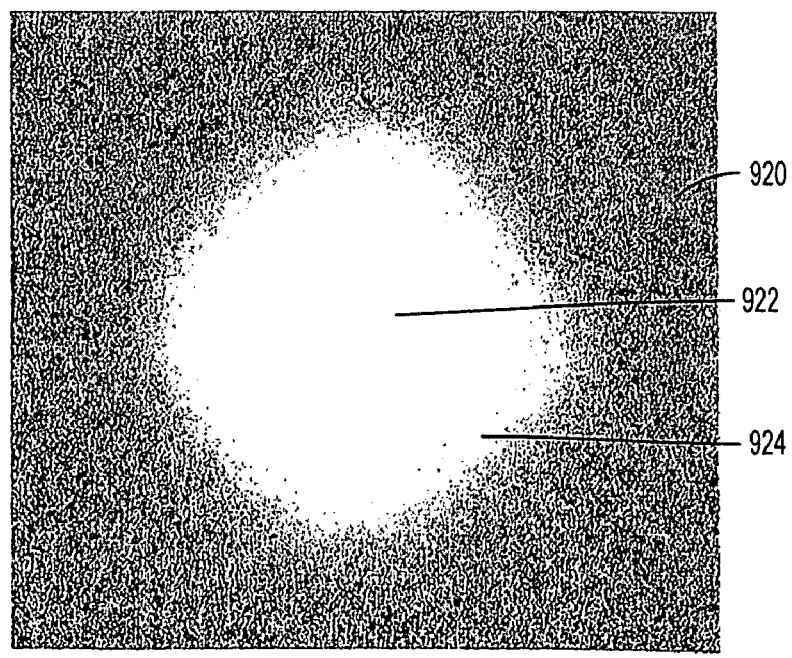
FIG. 9B is an image of the exemplary illuminated area of FIG. 9A, wherein the projected image of the array is defocused.

Referring to FIG. 3B, lensing 130 is so configured that its focal point, identified as 510, is behind array 605. Thus, at an incident area at the same distance as in FIG. 3A, a defocused image 501, providing a relatively distinct zone of illumination, but not reflecting the pattern of array 605, is projected. The illuminated area of image 501 is larger than the focused image 500 shown in FIG. 3A, and has a higher intensity of illumination. Image 501 has a generally rectangular form, as array 605 is generally rectangular. Examples of a projected focused image of an array and a projected defocused image of an array are shown in FIGS. 9A and 9B, respectively.

Referring to FIG. 3C, lensing 130 is so configured that the focal point 510 is in front of array 605. This arrangement provides a blurred image of the array, with indistinct edges, and great variation in intensity. The image provides less uniformity and lower intensity than the defocused image of FIG. 3B.

As illustrated in FIGS. 3A, 3B and 3C, relative to a focused image of an emitter array, a defocused image has a larger area, more even illumination, and a higher intensity of illumination. In an exemplary embodiment, an intensity of about 4000 foot-candles is obtained across a field. It will be appreciated that superposition of defocused images of multiple arrays results in both higher illumination intensity and better uniformity of illumination across the illuminated area.

Figure 6:
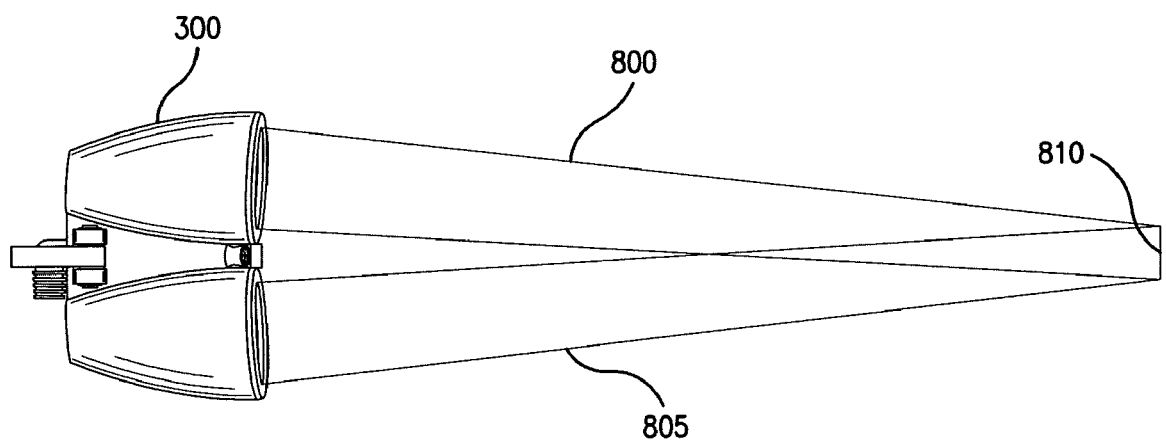
FIG. 6 is a partial top view of an illuminating assembly showing emitted light beams.

FIG. 6 is a partial top view of an illuminating assembly showing emitted light beams. Housing 300 is shown, with exemplary light beams 800, 805, emitted by devices within housing 300. Light beams 800, 805 intersect at incident area 810. Light beams 800, 805 project defocused images of respective emitting arrays, so that defocused images will appear on a surface positioned at incident area 810.

In one embodiment, for a particular application, an axis of each emitting device 100, 200 may deviate from parallel by an angle of between about 2 degrees and about 4 degrees, and in some embodiments about 2.24 degrees, depending on the distance between the devices and the distance from the devices to the incident area. Of course, the deviation from parallel may be greater or less, depending upon the distance between the emitting devices and the distance to the area to be illuminated. The axes of light beams 800, 805 similarly deviate from parallel.

Figure 4:
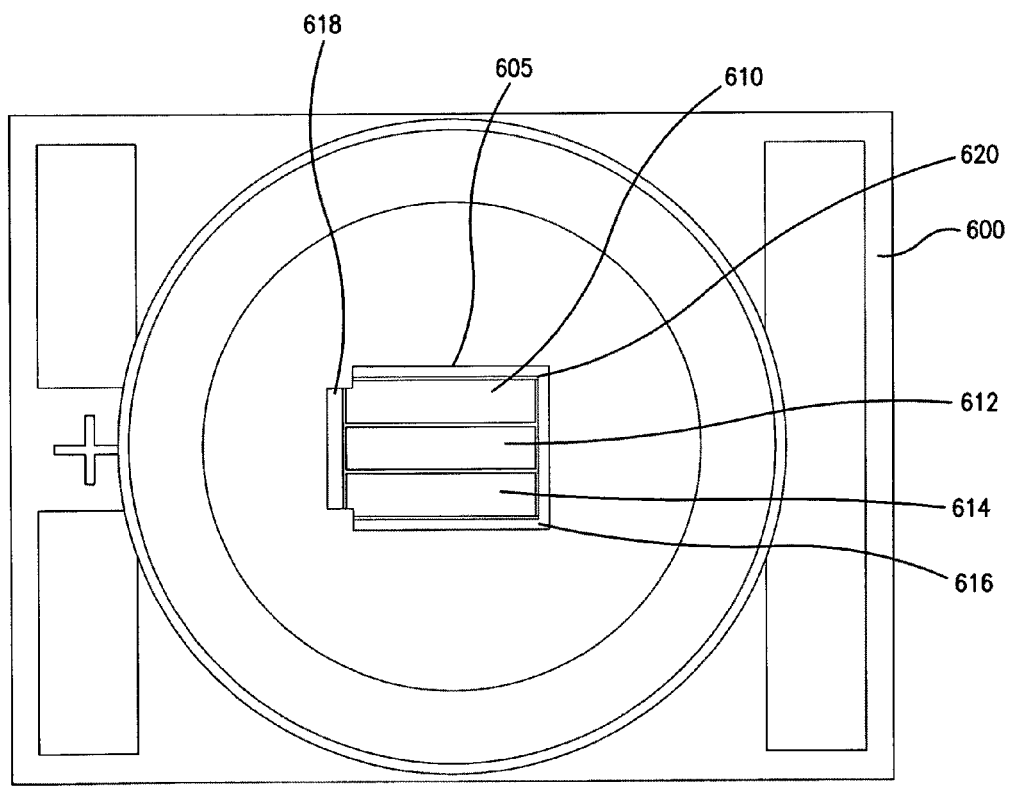
FIG. 4 is a top view of an LED, showing a shape of an array, usable in the illuminating assembly of FIG. 1.

Referring to FIG. 4, an exemplary LED emitter 600 is shown. By way of example, the LED may be a Cree XLamp High-Power LED, available from Arrow Electronics, Manalapan, N.J. An emitter array 605 is shown. Array 605 is a two-dimensional array, having an overall generally rectangular shape. The array 605 may be on a single die, or more than one die. Generally rectangular sub-arrays 610, 612, 614, and elongated sub-arrays 616, 618 emit light. Those subarrays may include individual diode elements, which are relatively closely spaced together, such as at 400 dots per inch (dpi) or 1200 dpi. Array 605 does not emit from relatively narrow areas 620, which may contain controllers and other devices, for example.

It will be appreciated that a focused projection of array 605 will result in a corresponding image, with the projections of subarrays 610, 612, 614, 616 and 618 being bright, with dark lines corresponding to areas 620. Furthermore, there may be variations in light output intensity within sub-arrays. Such variation may occur as a result of errors in manufacturing of the LED sub-array. As a result of the pattern and variations in intensity, if a focused image of array 605 is projected on an incident area, there will be substantial variations in illumination intensity. By projection of a defocused image, variations in illumination intensity are reduced. In addition, variations in illumination intensity may be reduced by superposing images from two or more light emitting devices.

For example, FIG. 9A is an image of an exemplary illuminated area showing a substantially in focus projected image of an emitting array. FIG. 9B is an image of the exemplary illuminated area of FIG. 9A, wherein the projected image of the array is defocused. Referring to FIG. 9A, an exemplary projected image 900 is shown. Image 900 is substantially in focus. Image 900 is an image that may be projected by an arrangement such as that shown in FIG. 3A. Image 900 includes regions of relatively high illumination intensity, such as at 905, that are a projection of emitting areas of the array, and relatively low illumination intensity, such as at 910, that are a projection of non-emitting areas within the array. Referring to FIG. 9B, an image 920 showing a defocused image of a rectangular array is illustrated. Image 920 is an image that may be projected by an arrangement such as that of FIG. 3B. Image 920 is substantially rectangular as a result of the rectangular shape of the array. As a result of defocusing, the illumination intensity is more uniform than in image 900 of FIG. 9A. Still referring to FIG. 9B, image 920 has a high illumination intensity area, or hotspot 922, at the center of image, and extending outward from the center of the image. A zone 924 in which illumination intensity gradually decreases with distance from the center of the image surrounds hotspot 922.

It will be appreciated that superimposition of defocused images of multiple arrays may further reduce variations in illumination intensity.

Figure 10:
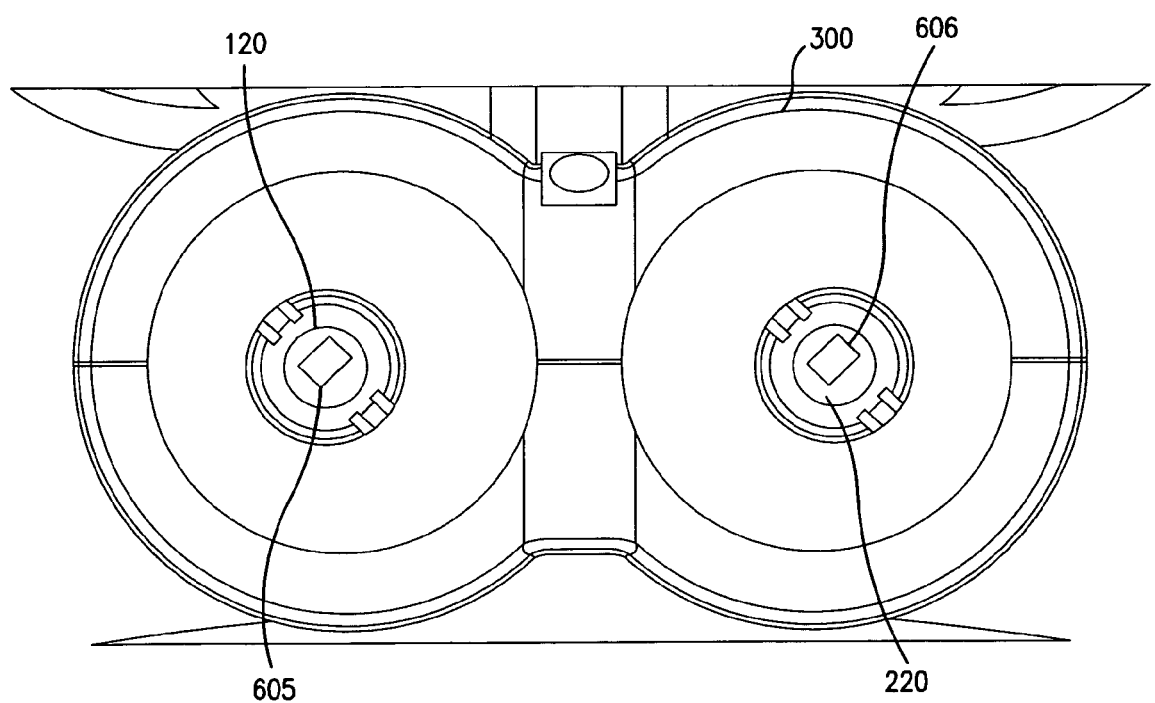
FIG. 10 schematically illustrates a relationship between emitting arrays and other components of an illuminating assembly in an embodiment.

Referring to FIG. 10, an exemplary orientation of emitter arrays relative to an assembly will be discussed. Housing 300 has a generally transverse axis, which is horizontal when assembly 10 is positioned for use. The positions of LED's 120, 220 are shown. The orientations of emitter arrays 605 are shown, somewhat schematically. Generally rectangular emitter arrays 605 are oriented so that their sides are at an angle of substantially 45 degrees to the transverse axis. In this exemplary orientation, an area illuminated at a selected distance from the assembly may have a wider range in a horizontal direction than an area so illuminated if the rectangular array is oriented otherwise. It will be appreciated that other orientations of emitter arrays, as well as other shapes of emitter arrays, may be provided.

Figure 5:
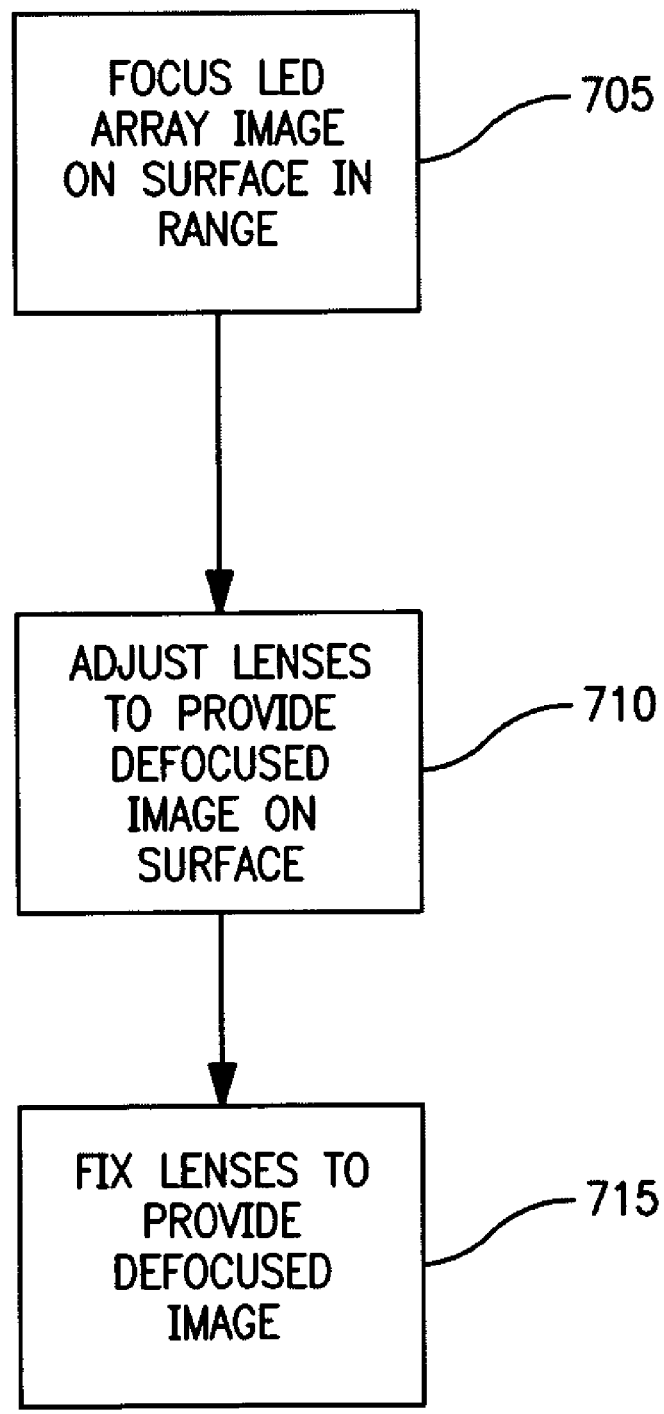
FIG. 5 is a process flow diagram of a method of preparing an illuminating assembly.

Referring to FIG. 5, a method for preparing an illumination assembly will be described. In a method, an incident plane, such as an opaque sheet, is placed at a desired distance from an illumination device, such as illumination device 100 or 200. The illumination device is activated, and an image from an emitting array in the illumination device is then focused on the sheet, as indicated by block 705. The projected image of the emitting array may appear to include more than one distinct illuminated area, and may have relatively sharp edges. The lens or lenses are then adjusted until an unfocused or defocused image of the array is obtained, as indicated by block 710. Lens adjustment may include changing the distance between a lens and the array, changing the distance between lenses, substituting different lenses, or adding or removing lenses. The adjustment step may include adjusting lenses so that the focal point of the lens or lenses is behind the array. A light meter may be positioned at the desired distance, and the lenses may be adjusted until the illumination intensity detected by the light meter is substantially at a maximum. With each lens adjustment, the area of illumination at the selected distance may also be checked to determine if the area is the minimum desired size. It will also be appreciated that different LED's may be selected.

Figure 8:
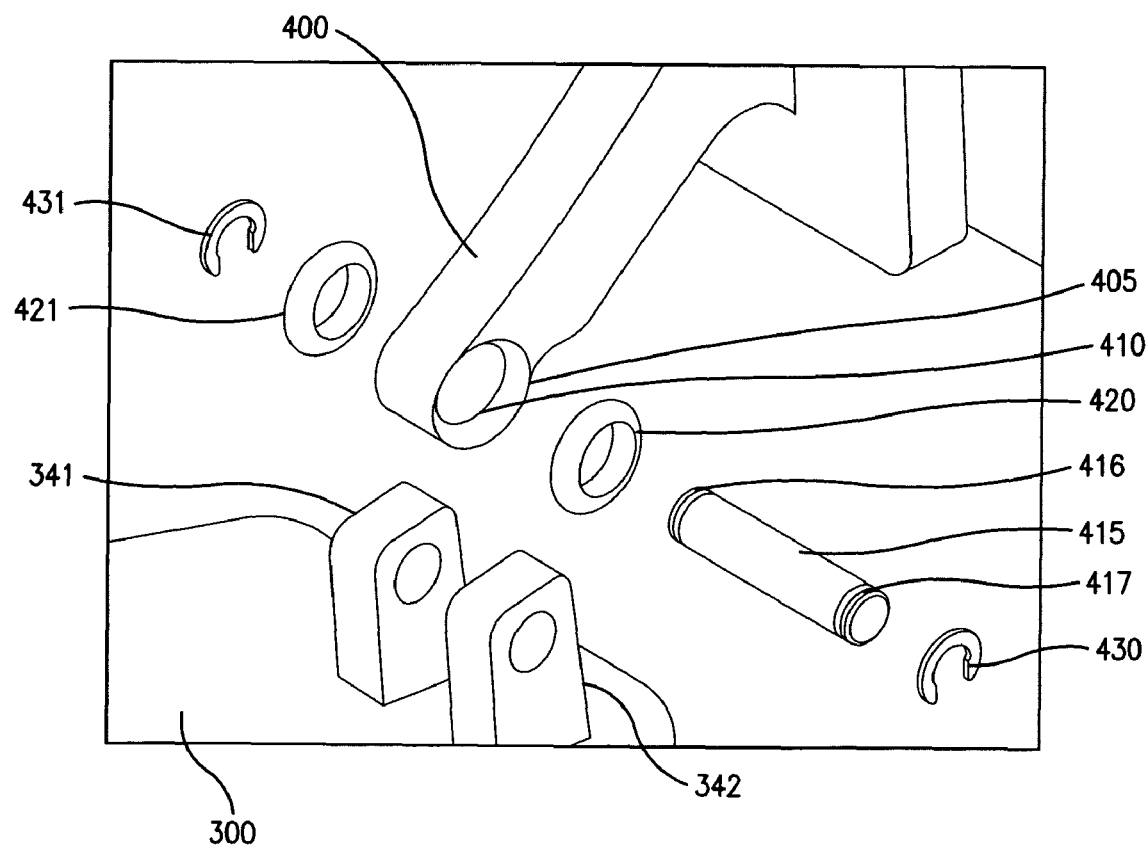
FIG. 8 is an exploded view of connectors between a housing and a bracket in the illuminating assembly of FIG. 1.

Referring to FIG. 8, an exemplary connecting arrangement between housing 300 and bracket 400 is shown in an exploded view. Bracket 400 has bore 405 which receives shaft 415. Bracket 400 has wells 410 around the openings of bore 405. O-rings 420, 421 are received in wells 410, which may be contoured to partially match the outer generally circular shape of O-rings 420, 421. O-rings 420, 421 have a thickness greater than a depth of wells 410. Accordingly, when O-rings 420, 421 are positioned in wells 410, and bracket 400 is positioned so as to align bore 405 with and between bores in upstanding arms 341, 342, O-rings 420, 421 are in contact with arms 341, 342. O-rings 420, 421 may prevent relative movement of bracket 400 and housing 300. O-rings 420, 421 may be of rubber, for example. Shaft 415 is received in bore 405, O-rings 420, 421, and the bores in arms 341, 342. Retaining rings 430, 431 engage grooves 416, 417 in shaft 415, and prevent shaft 415 from working loose.

It will be appreciated that obtaining illumination at a selected distance, and over an illuminated area of a selected size, involves multiple mounting interrelationships. Relationships that are included are the angle between the horizontal plane of the housing 300 and the head band 400, which may be changed by rotation of housing 300 around the connection shown in FIG. 8. A further relationship is the mounting of illumination 100, 200 in housing 300. Illumination devices 100, 200 are mounted so as to emit at an angle from an axis relative to normal to the housing 300. As this angle is increased, then the selected distance is correspondingly smaller. This angle may be altered by rotating the emitter mount about the pins of housing 300, or by selecting an emitter mount having a closed surface in a plane at a selected angle to the axis of the housing pins.

It will be appreciated that many variations are possible. For example, the illumination devices need only have their relative orientation fixed, and need not be within a housing. More than illumination devices may be employed. For example, a total of four illumination devices may be provided, in fixed relative positions in a housing, and all causing emitted beams to intersect at a selected distance from the assembly.

While the foregoing invention has been described with reference to the above described embodiments, various modifications and changes can be made without departing from the spirit of the invention. Accordingly, all such modifications and changes are considered to be within the scope of the invention.

What is claimed is:

1. An assembly for providing illumination to an incident area comprising:
   (a) a support;
   (b) a first illumination device coupled to the support, the first illumination device including a first light emitting device and a first lens positioned for focusing light emitted by said first light emitting device;
   (c) a second illumination device coupled to the support, the second illumination device including a second light emitting device and a second lens positioned for focusing light emitted by said second light emitting device;
   (d) the first and second lenses projecting defocused images of the respective first and second light emitting devices to the incident area.

2. The assembly of claim 1, wherein said first and second light emitting devices comprise light emitting diodes.

3. The assembly of claim 2, wherein said light emitting diodes comprise two-dimensional arrays.

4. The assembly of claim 3, wherein said arrays are substantially rectangular, and said assembly is so mounted that said arrays are positioned with their sides at substantially a 45 degree angle relative to horizontal when positioned for use.

5. The assembly of claim 3, wherein said first and second lenses are configured having a focal point behind said arrays.

6. The assembly of claim 1, wherein said first illumination device comprises a housing supporting said first lens and said first light emitting device.

7. The assembly of claim 1, further comprising a headband coupled to said support.

8. The assembly of claim 1, wherein said support comprises a main housing encompassing said first and second light emitting devices.

9. The assembly of claim 8, wherein each of said first and second light emitting devices comprises an emitter mount directly coupled to said main housing, and a light emitting diode on said emitter mount.

10. A method of illuminating a target area a selected distance from a light emitting assembly, comprising:
 (a) providing a first emitting array in the light emitting assembly;
 (b) providing a second emitting array in the light emitting assembly:
 (c) projecting a defocused image of the first emitting array to the target area; and
 (d) simultaneously projecting a defocused image of the second emitting array to the incident area.

11. The method of claim 10, wherein said first and second arrays are light emitting diode arrays.

12. The method of claim 11, wherein said arrays are two-dimensional.

13. The method of claim 11, wherein said projecting steps comprise employing lens assemblies associated with each of the arrays.

14. The method of claim 13, wherein said arrays are substantially rectangular and are positioned during said projecting steps with their sides at substantially a 45 degree angle relative to horizontal.

15. A method of preparing an illumination assembly having at least one emitter array for illuminating a target area a selected distance from an output of the assembly, comprising:
 (a) projecting an image of the at least one emitter array through a focusing lens assembly to a surface at the selected distance;
 (b) adjusting the lens assembly to focus the projected image on the surface; and
 (c) adjusting the lens assembly to defocus the projected image.

16. The method of claim 15, wherein the emitter array is a light-emitting diode array.

17. The method of claim 15, wherein the array is on a single die.

18. The method of claim 15, wherein said adjusting step comprises positioning the focal point of the focusing lens assembly behind the emitter array.

19. An illumination device, comprising:
 a light emitting device; and
 a lens positioned for focusing light emitting by the light emitting device, the lens configured so as to project a defocused image of light emitted by the light emitting device.

20. The illumination device of claim 19, wherein the light emitting devices comprises a two-dimensional light emitting array.

21. The illumination device of claim 20, wherein the light emitting array is a light emitting diode array.

22. The illumination device of claim 19, wherein the lens has a focal point, the light emitting device being between the focal point and the lens.

23. The illumination device of claim 22, wherein the light emitting array is a two-dimensional light emitting diode array.

24. The illumination device of claim 23, wherein the array is on a single die.

\* \* \* \* \*